(12) United States Patent
Haas et al.

(10) Patent No.: US 6,440,059 B1
(45) Date of Patent: Aug. 27, 2002

(54) MAGNETOHYDRODYNAMIC CARDIAC ASSIST DEVICE

(75) Inventors: Michael J. Haas, Covington; Richard Bailey, Mandeville, both of LA (US)

(73) Assignee: Cimex BioTech LC, Covington, LA (US)

(*) Notice: Subject to any disclaimer, the term of this patent is extended or adjusted under 35 U.S.C. 154(b) by 0 days.

(21) Appl. No.: 09/418,236

(22) Filed: Oct. 14, 1999

(51) Int. Cl.$^7$ ................................................. A61M 1/10
(52) U.S. Cl. ................................... 600/17; 600/9; 607/3
(58) Field of Search ............................... 600/16, 17, 9, 600/15; 623/3.1, 3.27, 3.28, 3.11; 607/1, 3

(56) References Cited

U.S. PATENT DOCUMENTS

| | | |
|---|---|---|
| 2,612,109 A | 9/1952 | Wakefield |
| 2,925,814 A | 2/1960 | Vibber et al. |
| 3,066,607 A | 12/1962 | Cole |
| 3,206,768 A | 9/1965 | Preston |
| 3,568,214 A * | 3/1971 | Goldschmied .................. 128/1 |

(List continued on next page.)

FOREIGN PATENT DOCUMENTS

JP          2000-37463 A  *  8/2000

OTHER PUBLICATIONS

Vasil'eve, Critical Parameters of a Seawater Conduction MHD Accelerator, Magnitnaya Gidrodinamika, Jan. 1985.
Gural, Nguyen and van den Bergh, Conceptual Design of A Superconducting MHD Propulsion System, Supercollider 4, 1992.
Bardy et al; Some Factors Affecting Bubble Formation with Cathether Mediated Defibrillator Pulses; Circulation, vol. 73, No. 3, Mar. 1986.
Moulder; Static Electric and Magnetic Fields and Human Health: Questions and Answers; MCW.EDU Internet web site Jan. 26, 1999.
Moulder; Static EM Fields & Cancer Faq's; ; jmas.co.jp web site Jan. 26, 1999.
American Heart Association, Basic Support for Healthcare Providers; Copyright 1997.

*Primary Examiner*—Kennedy Schaetzle
(74) *Attorney, Agent, or Firm*—Joseph T Regard Ltd

(57) ABSTRACT

A left ventricular assist device (LVAD) utilizing MHD principles, wherein an aortic electrode assembly is located within a main femoral artery in the aorta, in the vicinity of the heart of a patient, which electrode assembly is exposed to a high density magnetic field generated outside of the patient. The high density magnetic field urges electrified blood within the artery in the vicinity of the electrode along the length of the electrode in a uniform direction, thereby providing a fluid pumping force and pressure commensurate with the magnetic field strength and electrode current in accordance with MHD theory and practice. A cardio bypass system is also taught, wherein in addition to the aortic electrode assembly, as second electrode assembly is placed in the inferior vena cava having an opposite electrode polarity to the aortic electrode assembly, such that the second electrode assembly directs blood flow toward the heart. In the preferred embodiment of the invention, the magnetic field is generated exterior of the patient via a superconducting magnet which is designed to bridge the torso of the patent, such that the electrodes are generally centrally disposed within the magnetic field, along a longitudinal axis aligned with the aorta (and inferior vena cava), and generally orthogonal to the magnetic field. Sensors monitoring the patient may utilize ECG, blood pressure, and other data to control the magnet, varying the magnetic field so as to emulate the pumping action and intensity of the patents heart in real time, or simulate same.

36 Claims, 15 Drawing Sheets

U.S. PATENT DOCUMENTS

| | | | |
|---|---|---|---|
| 3,633,217 A | * 1/1972 | Lance | 623/3.19 |
| 3,757,846 A | * 9/1973 | Herman, Jr. | 164/51 |
| 4,252,605 A | 2/1981 | Schaffer | |
| 4,265,680 A | 5/1981 | Pelser et al. | |
| 4,838,850 A | 6/1989 | Rosengart | |
| 5,003,517 A | 3/1991 | Greer, Jr. | |
| 5,220,841 A | * 6/1993 | Brown et al. | 73/861.12 |
| 5,385,581 A | 1/1995 | Bramm et al. | |
| 5,470,208 A | 11/1995 | Kletschka | |
| 5,668,420 A | 9/1997 | Lin et al. | |
| 5,685,698 A | 11/1997 | Smoll | |
| 5,685,700 A | 11/1997 | Izraelev | |
| 5,762,599 A | 6/1998 | Sohn | |
| 5,763,951 A | 6/1998 | Hamilton et al. | |
| 5,851,174 A | 12/1998 | Jarvik et al. | |
| 5,888,241 A | 3/1999 | Jarvik | |
| 5,891,134 A | 4/1999 | Goble et al. | |
| 5,911,685 A | 6/1999 | Siess et al. | |
| 5,928,131 A | 7/1999 | Prem | |
| 6,053,873 A | * 4/2000 | Govari et al. | 600/505 |

\* cited by examiner

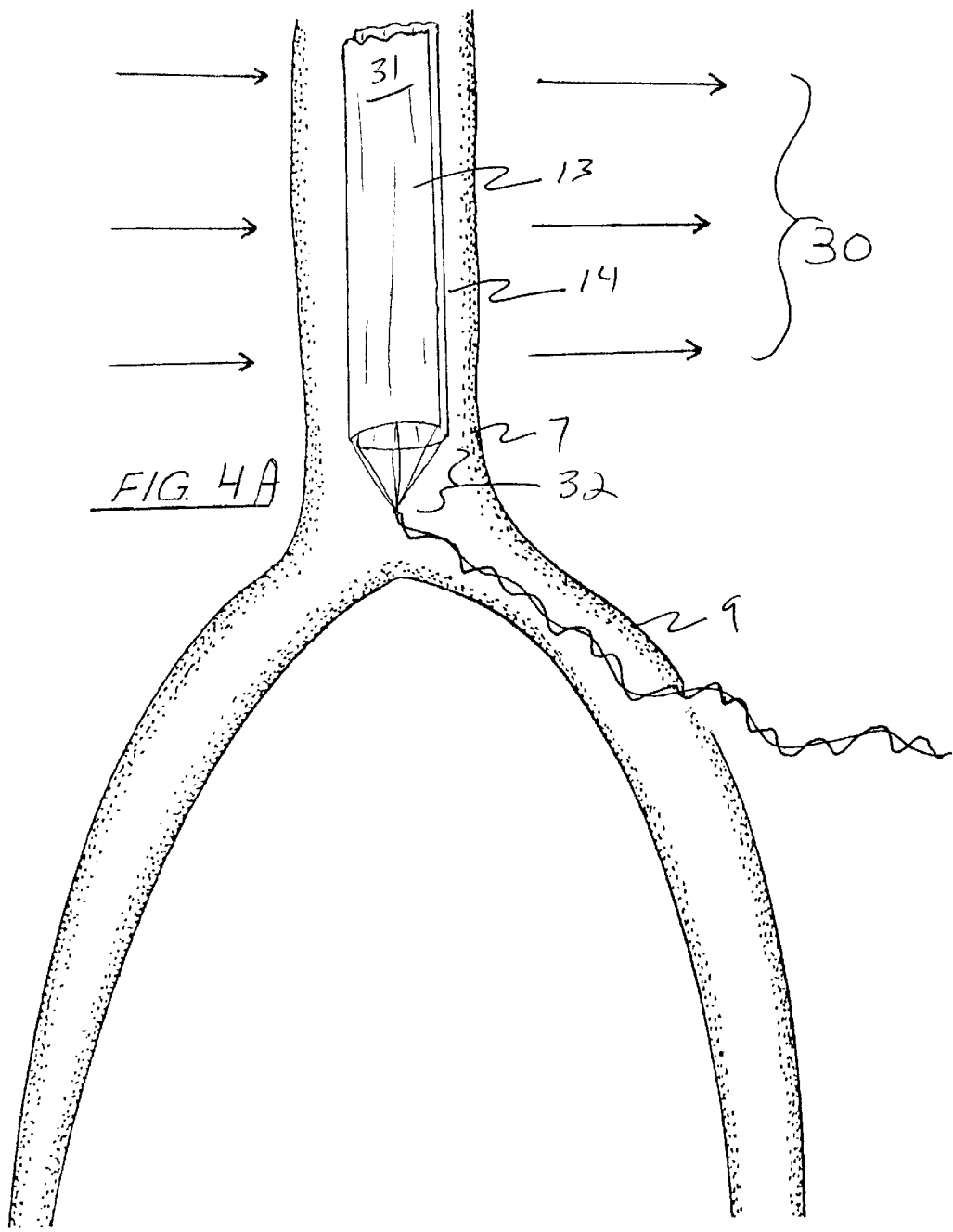

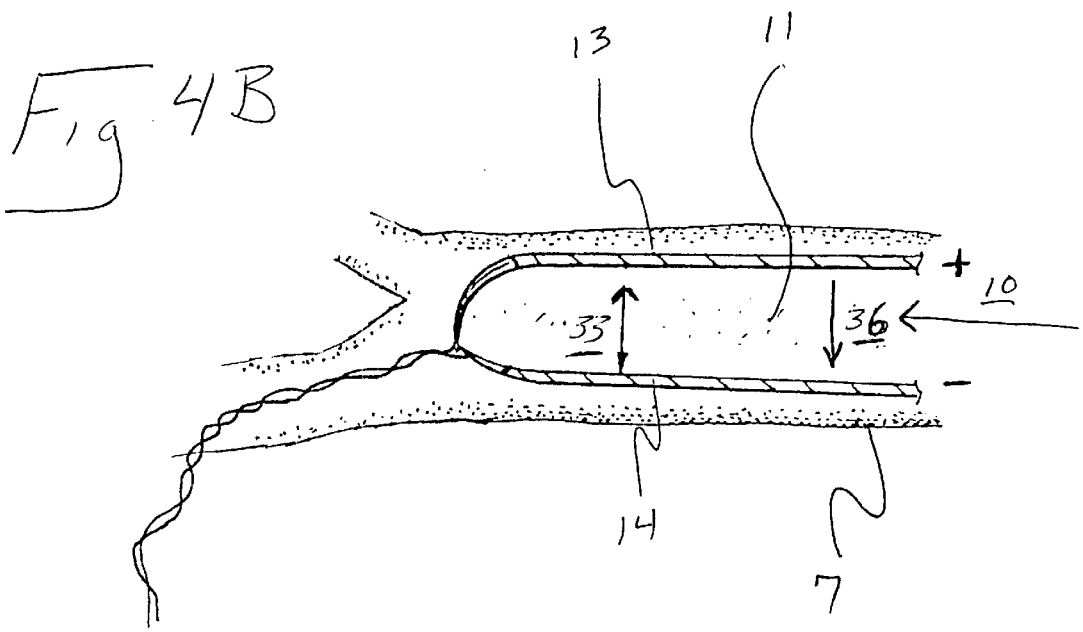
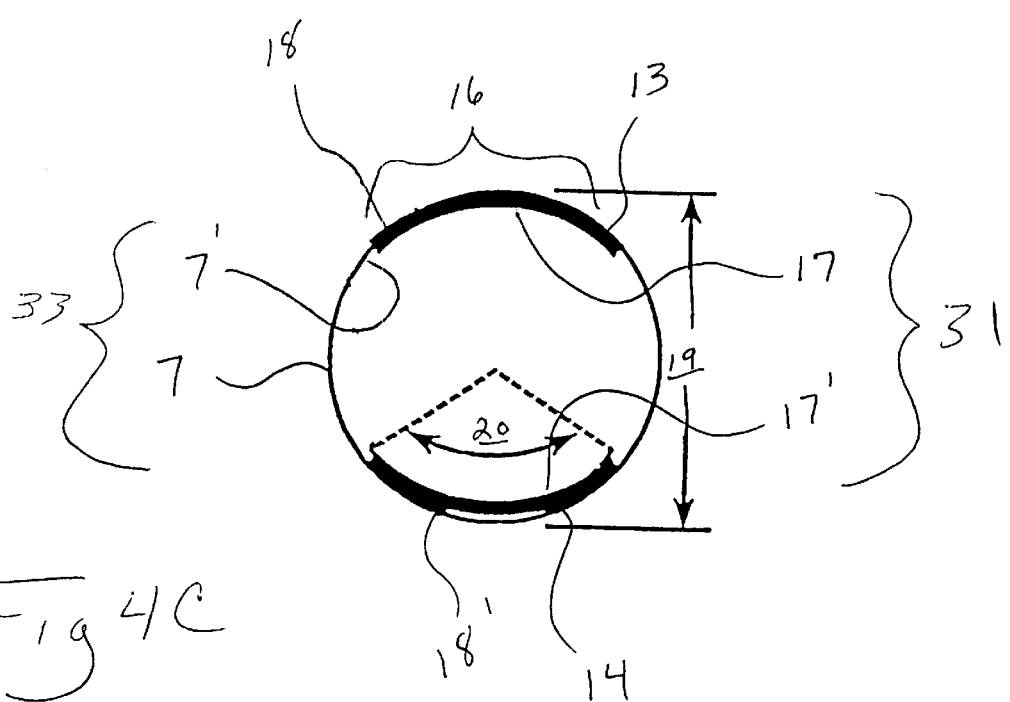

Pump pressure, Ringers
7 Tesla, 2 cm by 10 cm pump

Pump Pressure, Saline
7 Tesla, 2 cm b 10 cm pump

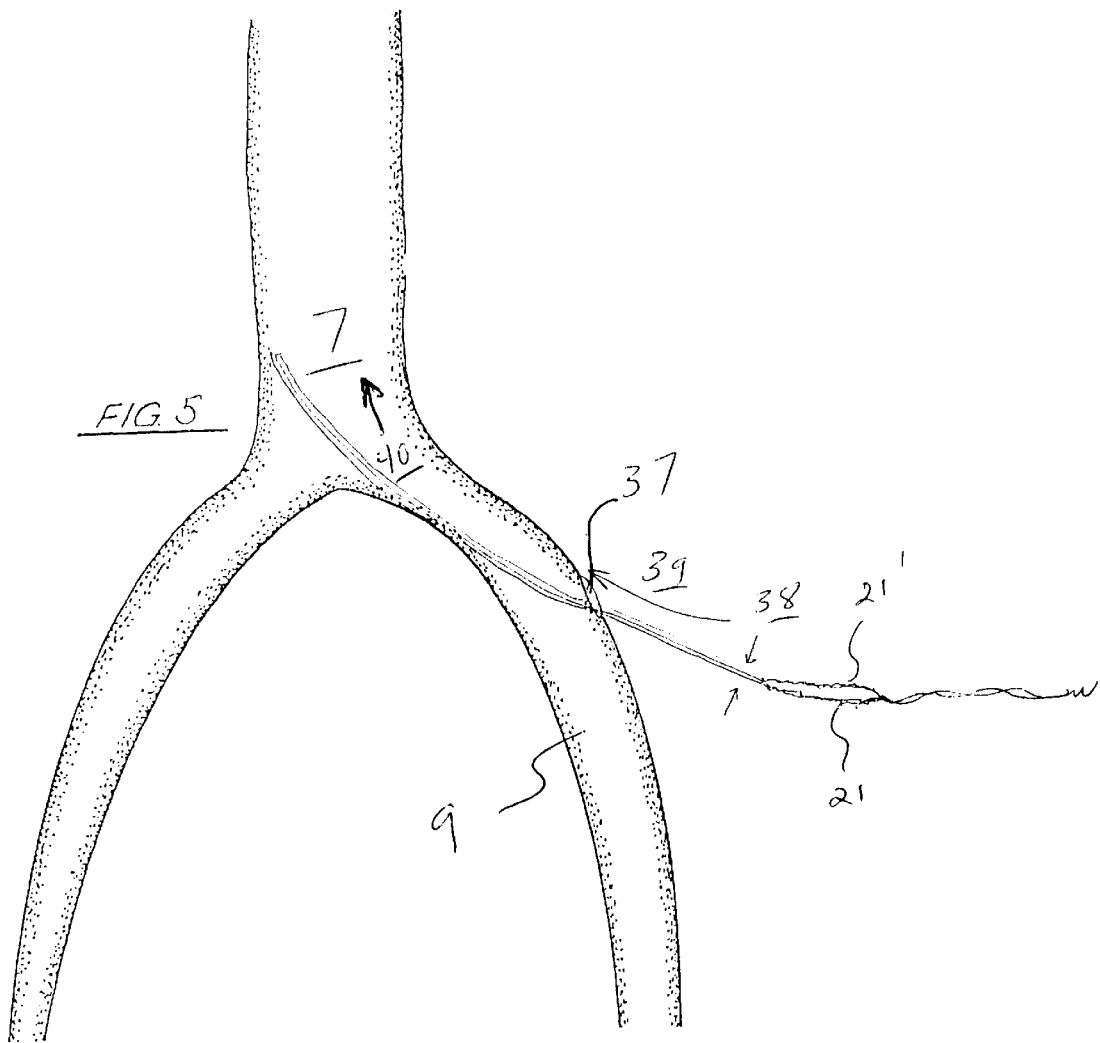

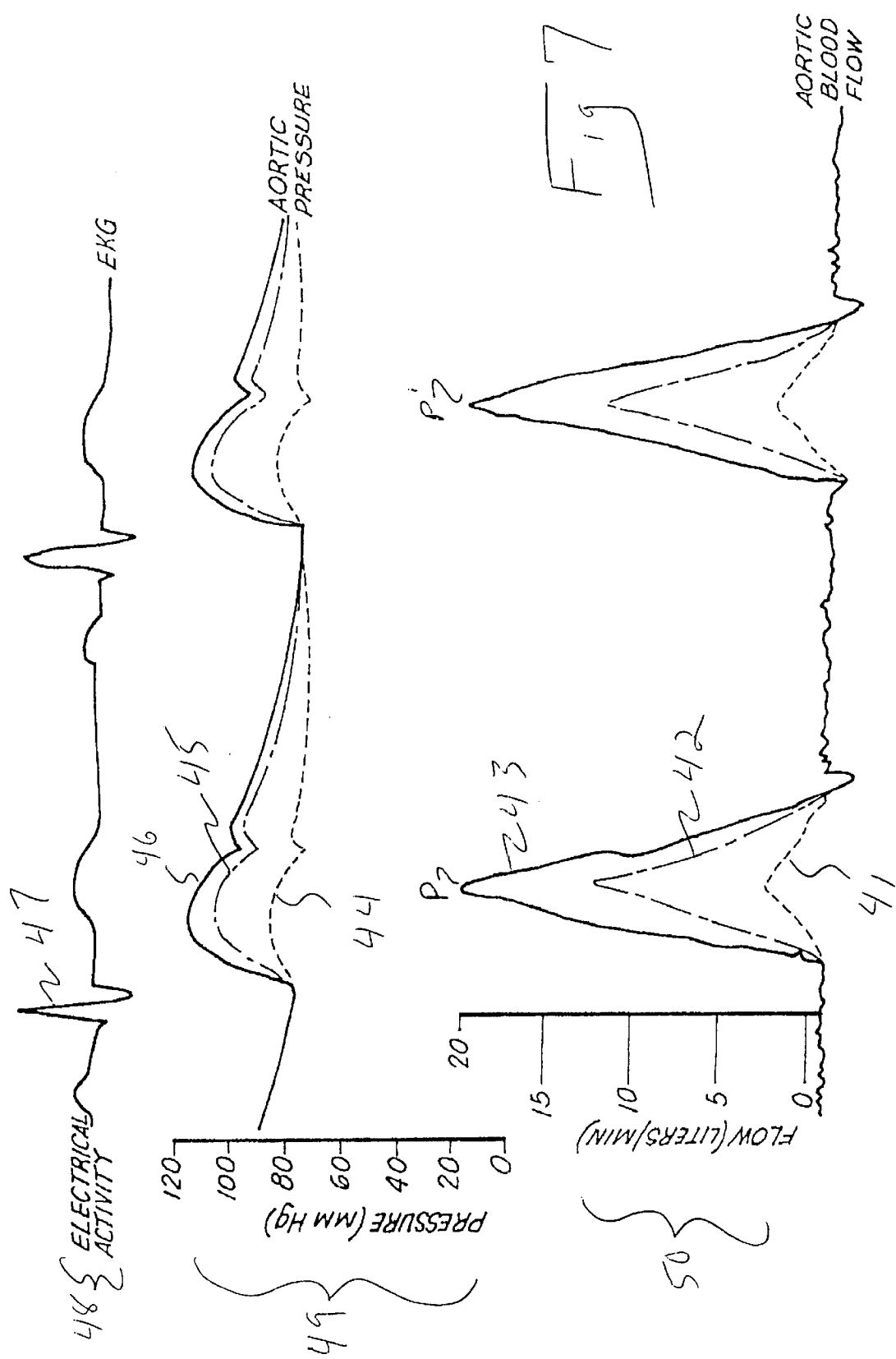

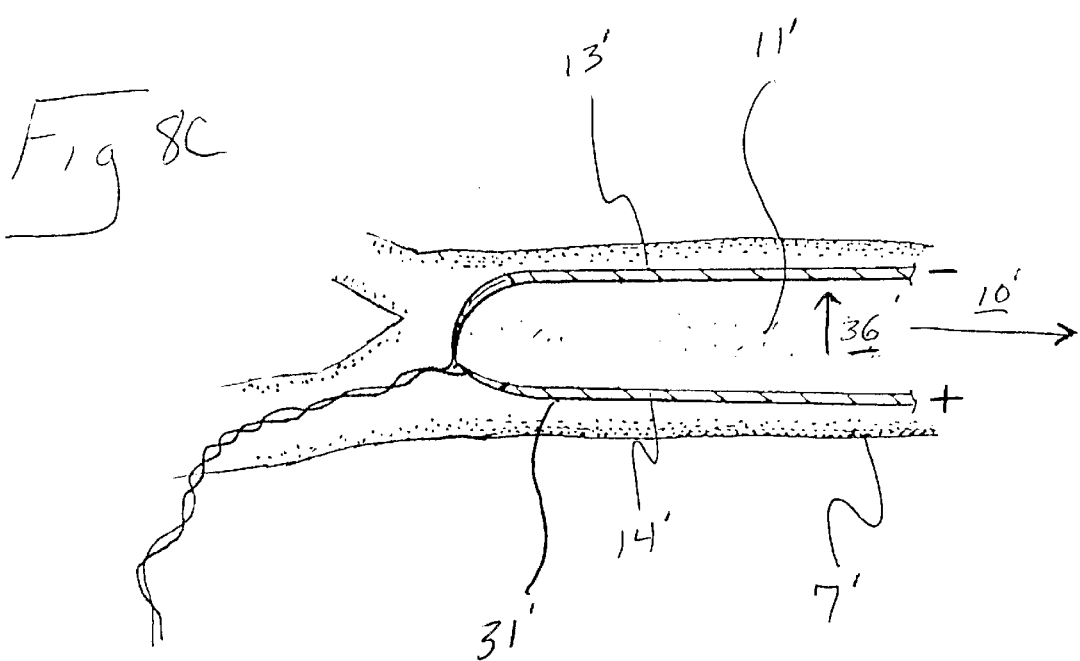

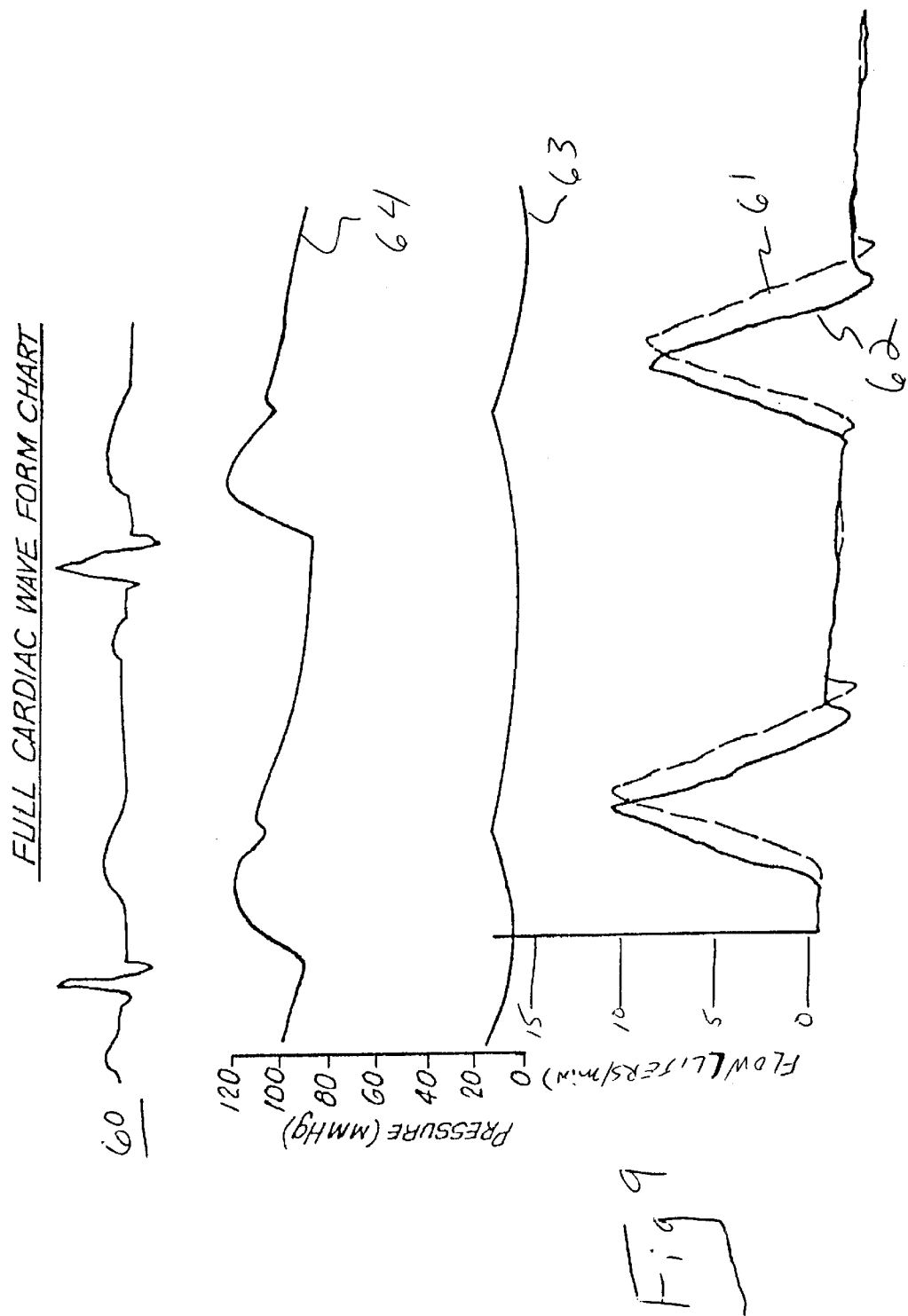

MAGNETOHYDRODYNAMIC CARDIAC ASSIST DEVICE

TECHNICAL FIELD OF THE INVENTION

The present invention relates to cardiac assist devices, and in particular to a magnetohydrodynamic (MHD) heart pump which is less intrusive, and more effective, and easier to implement than prior art designs. The system of the present invention has no moving parts to wear out or break down, and is far less invasive than prior art systems.

The preferred embodiment of the present invention contemplates a cardio assist device utilizing MHD, wherein first and second, parallel electrodes forming an electrode assembly are placed, via the patient's femoral artery, into the aorta in the vicinity of the abdomen, which electrode assembly is exposed to a high density magnetic field generated outside of the patient. A current generated by a control unit energizes the first and second electrodes, and the blood situated therebetween, causing the high density magnetic field to interact with the energized blood, hydrodynamically motivating said blood to flow through the electrode assembly, in a uniform direction, thereby providing a fluid pumping force and pressure commensurate with the product of the magnetic field strength and the induced current in the blood vessel in accordance with MHD theory and practice, the general operational theory of which was first understood and explained by Scottish physicist James C. Maxwell in the mid-19th century.

In the preferred embodiment of the invention, the magnetic field is generated exterior of the patient via a superconducting magnet which is designed to produce a large magnetic field in the middle torso of the patient, so that the electrode assembly is generally centrally disposed within the magnetic field, along a longitudinal axis aligned with the aorta (and/or vena cava), and with electrode current flow generally orthogonal to the magnetic field.

Sensors monitoring the patient may utilize electrocardiogram (ECG), blood pressure, and blood flow, and other data to control the current in the blood in order to vary the pumping pressure and flow, so as to emulate the pumping action and intensity of the patients heart in real time, so as to lessen the trauma of artificial pumping assistance, or bypass on the patient.

The present device may also be utilized to provide full cardiac blood flow, as when a heart is stopped for bypass surgery, or to provide targeted limb or organ perfusion in a patient.

BACKGROUND OF THE INVENTION

Nearly one million acute cardiac failure fatalities occur each year in the U.S., many of which would have been preventable if there had been developed a suitable artificial heart. Heart assist or left ventricular assist devices (LVADs) are currently large, very invasive (requiring major chest surgery) and represent a significant patient risk.

These pumps require surgery to implant tubes, wires and other large devices to provide the motive pumping power which normally enters and exits the body cavity in the chest area. Typically large and percutaneous devices, they represent a significant surgical risk in their implementation, even if they do provide the necessary coronary assistance. Removing these devices requires another major bout of surgery with the attendant risks.

Another problem with current LVAD devices is the possibility that the quality of circulation provided by the units, which lack the sophistication of being able to emulate the natural rhythm of the heart, are that they may provide insufficient blood flow to the brain or other organs, to the extent that serious medical consequences arise. Finally, most of the LVAD pumps currently in use cause some destruction of red blood cells due to the destructive mechanical pumping means utilized.

A plethora of artificial heart designs have been contemplated and tested, including:

Cardio-pulmonary bypass machines, which are utilized in bypass surgery when the heart is stopped and the pumping action is taken over by a machine exterior from the patient that uses a mechanical pumping action such as a roller pump. These machines are for temporary use only, and require extensive thoracic invasion and medication for implementation and use. Long term use would be fatal, and even short term use can result in hemorrhaging, infection, renal failure, stroke, and other serious effects.

An Archimedes type screw device was available for some time that was inserted in the femoral artery and advanced into the Aorta as a type of mechanical LVAD. It would spin fast and propel blood along the length of the Aorta toward the feet.

An intra-aortic balloon pump (IAPB) has been around for about 20 years. It is inserted in the Aorta blown up partially obstructing the aorta when the heart pumps. This helps preserve the heart and brain blood flow in times of low cardiac output by lowering the afterload on the heart and increasing flow to the coronary arteries and carotid arteries.

Artificial hearts are generally mechanically similar to the mechanical LVADs, but are configured to replace the entire heart (both the left and right side). These devices have been implemented both internally and externally, but with likewise unsatisfactory results.

All of the above devices are very invasive, requiring massive and lengthy thoracic surgery . The support equipment for these pump designs generally require chest penetrations and significant cardiac trauma for installation, sometimes including penetration of the heart itself. Lastly, the mechanical pumping action in all of the above designs is believed to cause damage to the blood constituents.

A list of patents which may have some pertinence to the present invention include:

| Patent Number | Inventor | Date of Issue |
| --- | --- | --- |
| 5911586 | Siess et al | 06/15/1999 |
| 5891134 | Goble et al | 04/06/1999 |
| 5888241 | Jarvik | 03/30/1999 |
| 5851174 | Jarvik et al | 12/22/1998 |
| 5763951 | Hamilton et al | 06/09/1998 |
| 5762599 | Sohn | 06/09/1998 |
| 5685700 | Izraelec | 11/11/1997 |
| 5668420 | Lin et al | 09/16/1997 |
| 5470208 | Kletschka | 11/28/1995 |
| 5385581 | Bramm et al | 01/31/1995 |
| 5003517 | Greer, Jr | 03/26/1991 |
| 4838850 | Rosengart | 06/13/1989 |
| 4265680 | Pelser et al | 05/05/1981 |
| 4242605 | Schaffer | 02/24/1981 |

U.S. Pat. No. 4,838,850 teaches an Electromedical Treatment Apparatus and which contemplates utilizing MHD effect to urge blood flow through blood vessels to increase circulation in targeted areas of the body. This patent does not contemplate the insertion of a device within the vasculature, but rather contemplates the use of magnetic lens to facilitate concentrated magnetic fields at a target area within the body, which may include a blood vessel, to utilize MHD effect to urge circulation of blood therethrough. (Col 7, lines 5–32).

U.S. Pat. No. 2,612,109 contemplates an earlier MHD pump design from the 50's.

U.S. Pat. No. 5,888,241 teaches a cannula pump driven by an impeller to assist the ventricals of the heart. The device comprises a tube which includes magnetic windings for driving the impeller.

See also 5,851,174.

U.S. Pat. No. 5,911,685 teaches an Intravascular micro axial pump which may be installed by advancing same through the patients vasculature, avoiding invasive chest surgery. The system incorporates an electrically driven, micro-motor having an impeller for pumping.

U.S. Pat. No. 5,385,581 teaches a Magnetically Suspended and Rotated Rotor in the form of a blood pump. This patent contemplates providing an impeller suspended and driven by a magnetic field, and includes feedback means in the form of sensors to monitor the patient, and computer control means to energize the coils with currents having frequency and amplitude adjusted in relation to the blood pressure at the pump inlet, so as to match the flow characteristics of the pump to physiological characteristics of the natural heart. Further, U.S. Pat. No. 5,928,131 also teaches a magnetically suspended, impeller driven heart pump with control means configured to simulate the beating of the patient's natural heart. See also U.S. Pat. Nos. 5,685,700 and 5,470,208, other magnetically suspended impeller systems configured to form blood pumps or the like.

U.S. Pat. No. 5,762,599 entitled "Magnetically-Coupled Implantable Medical Devices" teaches a variety of implantable devices, including pumps, valves, a bone stretching device, and an artificial sphincter which are driven by external drive magnets mounted for rotation externally about the subjects body, thus incorporating teachings of relevance to the present, searched for invention, although nonetheless distinguishable therefrom.

U.S. Pat. No. 5,891,134 teaches what may be considered to be the use of MHD technology to provide heat to tissue.

U.S. Pat. No. 5,763,951 teaches an MHD pump for a circuit board developed by Northrop Grumman.

U.S. Pat. No. 5,668,420 teaches an MHD propulsion system design for ships, submarines or the like utilizing a superconducting solenoid coil within a tube having a helical flow path, the system utilizing a coil configured to provide about 6–12 Tesla, and is provided as an example of this application, of which several patents have issued.

U.S. Pat. No. 4,265,680 issued 1981 teaches a Method of Making Hollow Magnetic Pipe for conveying conductive fluid in magnetohydrodynamic energy amplification systems; U.S. Pat. No. 4,252,605 also teaches a tube which may have MHD applications.

In summary, the prior art has contemplated blood pumps, artificial hearts, LVADs and the like relying upon mechanical pumping mechanisms which have included, for example, impellers, helical screws, bladders, pistons, vacuum, centrifugal, peristaltic pumps and the like. The above systems have considerable documented shortcomings including:

pumps incorporating an impeller design or the like tend to damage blood cells;

mechanical pumps have a limited life span which is not assured due to premature failure;

infection can be a problem, not only with the sterility of the unit itself, but also with the drive means, which often is exterior to the patient (ex. fluid driven heart pump);

the pumping action (hydrostatic pressures) can facilitate circulatory and red blood cell damage, renal failure, strokes, and a long list of other damaging effects;

the pumping action has limited capabilities for control and feedback, and generally cannot be satisfactorily varied to imitate the natural rhythm and flow of the heart; and internal pumps require massive invasion into the chest of the patient, and may require the complete severing and splicing a major artery to the unit.

Thus, there exits the need for a cardiac assist device which is minimally invasive and quickly implemented, providing a circulatory flow which is effective for life support, while being non-damaging to the patient.

GENERAL SUMMARY DISCUSSION OF THE INVENTION

The present invention utilizes magnetohydrodynamic technologies which have been proven for use in submarines and ships as propulsion systems, wherein first and second electrodes are employed along opposing walls of a conduit to provide a current flow through seawater situated therebetween. A superconducting, high field strength magnet is then employed to provide a high (known to be as high as 20 Tesla) magnetic field line of flux orthogonal to the current flow, which causes hydrodynamic forces upon the electrified seawater in accordance with Maxwell's equations, thereby pumping the seawater through the system with no moving parts or vibrations.

The present invention contemplates an adoption of this technology in a wholly new and different field, i.e., to provide an MHD cardiac assist device which is safe and effective to use, requiring minimal invasive surgery for implementation on a rapid basis, while providing a circulatory flow which is effective for life support.

Cardiovascular disease accounts for nearly 1 million deaths each year in the U.S. For many coronary patients, the heart could repair much of its own damaged muscle if part of the pumping effort were temporarily taken over by some assist device. If this assist device could be placed into and removed from the patient by way of their femoral blood vessels, for instance, the patient's heart blood flow could be maintained, as required, while reducing the physical load on the heart and allowing the injured muscle time to recover. This recovery period is expected to be from a few days to a few weeks, at which time the assist device would be turned off and removed from the patient.

The major advantage of the present invention, as compared to existing LVAD designs, is that the surgery risks to the already traumatized heart do not need to be taken. Rather, the present invention, an MHD-based LVAD uses the well established and relatively non-invasive catheter technology to install electrodes within a major blood vessel of the patient, well away from the heart, in order to facilitate blood flow. The present invention is designed for rapid, nominally invasive deployment, providing the urgent assistance needed by an acute cardiac failure patient, unlike the current support devices.

Installation of the system of the present invention could be performed in an emergency room, which frequently is where the temporary pumping assistance is often needed. The only additional equipment needed would be a high field magnet (not unlike current MRI magnets), and the special catheters and associated electronics to power the pump through small wires within the catheter structure.

In the present invention, the blood vessel pressure waveform can be modified specifically to avoid the problem of starving a specific organ due to reduced blood flow, by appropriate programming of the electronics that drive the pump, thus modifying the pressure during specific times of the periodic pumping cycle. Finally, most of the LVAD pumps currently in use cause some destruction of red blood cells. In contrast, the MHD pump of the present invention has no moving parts which should avoid the mechanical destruction of the blood components.

Existing LVAD devices require a large amount of electrical or pneumatic energy. Supplying this energy through percutaneous terminals or through an A.C. energy source and the attendant transformer through the skin coupling devices are the only alternatives available. Neither one of these alternatives is free from the risks of surgery and later infections, and supporting the mass of this equipment within the body cavity is a significant task.

By contrast, the pumping action of the MHD LVAD pump of the present invention is the result from the interaction of a high strength magnetic field generated by a magnet external to the patient, and a low level current conducted across the internal diameter of a blood vessel via a length of electrode. The electronics which drive the present pump would be external to the subject, and intrinsic electrical signals from the subjects heart used to synchronize the pumping signals utilizing cardiac signal sensors or commonly inserted ECG electrodes. Finally, the external magnetic field can be selected so that the current density in the blood stream is low enough to avoid excessive joule heating.

Heart assist devices should be designed to assist the heart while it repairs itself by taking over part of the hearts mechanical pumping work. The current technology of placing devices and tubes into and around the heart itself produces more traumatized heart muscle that must then be repaired by the hearts own resources in addition to the effort required to repair the damage that caused the initial need for emergency treatment.

In contrast, the present inventions technique of placing and removing the pumping device by the way of a major blood vessel using catheter technology eliminates trauma to the heart and the surrounding structure. If further surgery is required on the heart itself, the cardiac surgeon has a site with no scar tissue problems resulting from previous cardiac support device surgery.

Most heart patients, when the problem is the pump mechanism itself, are brought to a treatment center (hospital emergency room) and need immediate assistance or they will die. The use of drugs is of limited benefit, and an external heart/lung machine takes a lot of time to setup to take over the pumping task. The installation and implementation of a conventional LVAD requires major surgery as well as the use of a heart/lung machine during part of the operation. For an LVAD to be of maximum use in saving the life of a person with this class of heart trauma, the device must be implanted and started very quickly. Ideally, this should be accomplished in the emergency room itself, or in a nearby Intensive Care Unit containing the necessary equipment.

It is this unmet need for an immediate pumping aid, to allow time for the heart to repair itself, that the present invention provides, as indicated, without the need for invasive and risky thoracic surgery.

That the MHD pump of the present invention will pump a conductive liquid in the presence of a properly oriented magnetic field is beyond question, the technology already proven and successfully demonstrated, as discussed above, for an advanced submarine propulsion concept. Further, the drive technologies employed in the present invention is based upon a fundamental theory of magnetism developed by James C. Maxwell, namely, that a conductor containing a transverse magnetic field and an electrical current flowing orthogonal to this field will have a force applied upon the conductor which is proportional to the product of the current times the magnetic field strength. It is this fundamental principle which will allow the present invention to effectively and safely, without mechanical movement, hydrodynamically pump blood utilizing a simple electrode assembly situated within the blood vessel, in conjunction with a high field strength magnet which may be readily made utilizing presently available materials and technologies.

In addition to use as an LVAD, the system of the present invention may also be utilized to enhance limb perfusion in a variety of circulation disorders, including, for example, blood clots, thrombosis, frostbite, limb re-attachment, organ perfusion, carotid perfusion in cases of carotid artery spasm after angiogram, and increased profusion for acute stroke syndrome.

Another major intended use for this device is a by-pass pump support for coronary artery by-pass surgery. While electrodes in the abdominal aorta will provide a magnetohydrodynamic motive force away from the heart, one similarly placed in the Inferior vena cava of the abdomen with the electrodes oriented opposite the aortic ones will in turn pump blood toward the heart. With both electrodes energized and independently controllable, complete cardiac pumping action may be taken over for the heart just as it is currently done with a heart by-pass machine, but with major improvement.

Namely, with the present system, a profound advantage is created that gives surgeons the ability to perform lifesaving by-pass surgery without the need to grossly open the chest cavity. Current cardiac by-pass apparatuses require the chest cavity be opened to install large tubes into the heart and major blood vessels so that the blood can be removed from the body and circulated through a pumping machine. After external by-pass is established, then the heart can be stopped to allow repair of coronary blood vessels.

In contrast, in the MHD system of the present invention, the chest opening is not necessary to establish artificial circulation. The pump electrodes will be inserted through a blood vessel (s) such as the femoral artery and vein then the electrodes will be advanced into the aorta and inferior vena cava respectively. Electrode polarity will be such that the aorta has flow away from the heart and the inferior vena cava has flow toward the heart.

This push-pull action of the MHD pump will allow full blood flow at rest. Once this is in effect, much less invasive procedures can occur to repair coronary blood vessels such as through an endoscope. Through an endoscope the heart may be stopped electrically as is commonly done with open procedures, then coronary artery by-pass surgery procedures may be preformed. The heart would be restarted through an endoscope and the scopes removed.

By not opening the chest, patient's would not have to suffer through the risk, pain, and other problems associated with the current method of by-pass surgery such as: having their sternum cut in half, ribs stretched and broken, massive bleeding, life threatening scar tissue build up on the heart and internal chest cavity, blood pumped outside the body for support, lengthy invasive surgery, massive exposure of the internal chest to infection to just mention a few.

Therefore, it is anticipated that the present invention and system will reduce morbidity and mortality greatly from surgery such as a CABG (coronary artery bypass grafting) for the above reasons. One could make a similar comparison to medical improvement with the laproscopic way of performing gallbladder surgery verses the previous way of removing the gallbladder through a large incision in the abdominal wall. The older, what was termed "open", surgery would expose patients to a higher level of infection, more bleeding, pain, complications, longer procedure, and much longer recovery time. The "open" procedure would bring with it a six to eight week recovery time while with a laproscopic procedure a weekend of recovery is all that is necessary. In this case, as with a CABG, getting to the location to do the procedure is much worse than the procedure itself.

It is therefore an object of the present invention to provide a minimally invasive cardio pump which is quickly installed and effective in operation.

It is another object of the present invention to provide a cardio pump which has no moving parts and which pumps blood in such a fashion as to lessen the chances of damage to same.

It is another object of the present invention to provide a cardio pump which provides a pumping action which is based upon real time data from the heart of the patient, in order to optimize flow.

It is another object of the present invention to provide a cardio pump system wherein the electrodes are relatively inexpensive to manufacture and which may be disposable so as to provide maximum sterility.

Lastly, it is an object of the present invention to provide a method and system for cardiac heart assist utilizing magnetohydrodynamic drive utilizing a magnet exterior of the patient to generate a high density magnetic field about a portion of the torso of a patient, and a length of electrode placed within a major blood vessel of the patient within the magnetic field, in order to provide MHD flow of blood or other conductive fluid in the vicinity of the electrode, to support the heart of the patient.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 4A is an enlarged, top, partially cut-away view of FIG. 3, illustrating an exemplary electrode configuration comprising first and second, spread ribbon electrodes situated in spaced relationship, enveloping opposing anterior and posterior walls, respectively, of the aorta of the patient.

FIG. 4B is a side view of the invention of FIG. 4A, illustrating the spacing of the anterior and posterior electrodes within the aorta.

FIG. 4C is a cross-sectional view of the invention of FIGS. 4A and 4B, illustrating the positioning of the anterior and posterior electrodes within the aorta.

FIG. 5 is a top view of the method of installation of the electrodes into the patient, illustrating the electrodes being fed from the femoral artery of the patient into the abdominal artery.

FIG. 7 illustrates comparative ECG, Blood Pressure, and Blood Flow of an exemplary patient, as well as an exemplary LVAD assist waveform illustrating the patients condition with and without the LVAD assist of the present invention.

FIG. 8C is a cross-sectional view of the view of the invention of FIGS. 8A and 8B, illustrating the positioning of the anterior and posterior electrodes within the inferior vena cava, and associated polarities therewith.

FIG. 9 illustrates comparative ECG, Blood Pressure, and Blood Flow of exemplary, artificial waveforms of the present MHD pump system as used in a coronary bypass operation without the heart functioning, wherein electrode assemblies in the Aorta Vena Cava simulate the pumping of the heart.

DETAILED DISCUSSION OF THE INVENTION

Figure 1:
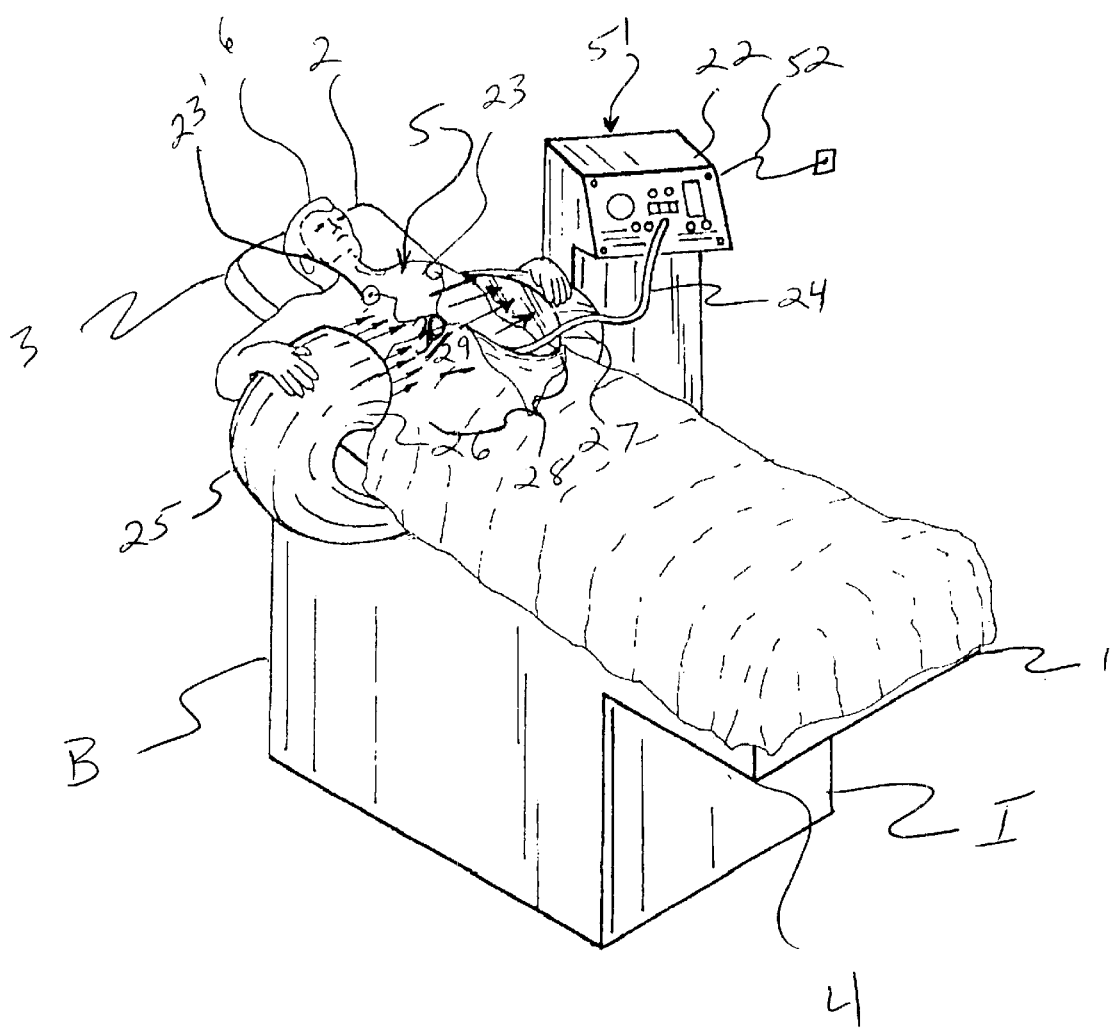
FIG. 1 is an isometric view of the preferred embodiment of the MHD cardio assist system of the present invention, illustrating a patient reclining within the exterior magnet, and further illustrating the computer control unit (CCU) controlling an electrode implanted within the patient.
Figure 2:
FIG. 2 is a side, partially cut-away view of the invention of FIG. 1, illustrating an electrode assembly implanted in the aorta of the patient, and a representative magnetic field generated by the exterior magnet of FIG. 1.
Figure 3A:
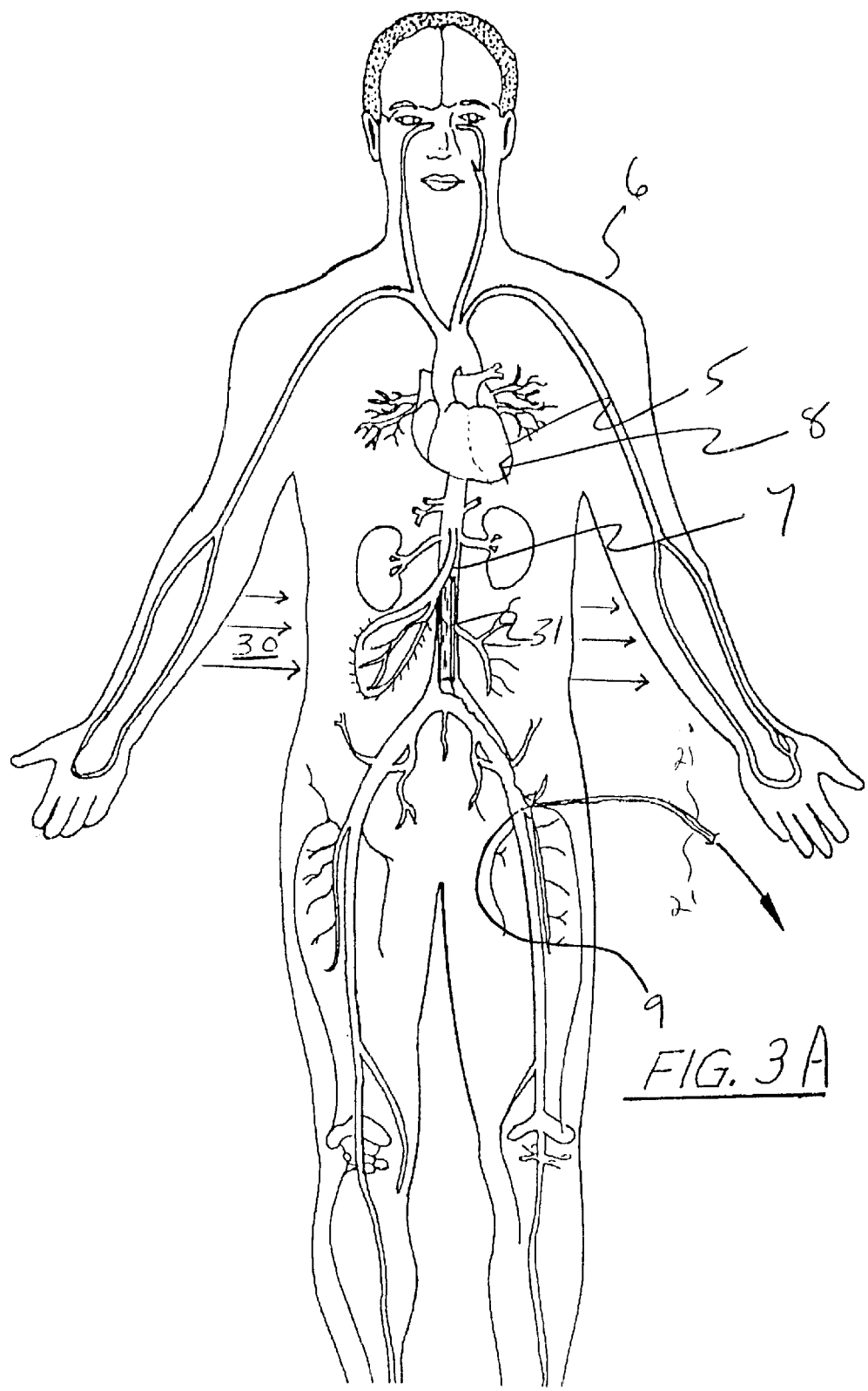
FIG. 3A is a top, partially cut-away view of FIG. 2, illustrating the electrode assembly implanted in the aorta of the patient, and the control wires passing therefrom, through the femoral artery, and out of the patient to be controlled by the CCU of FIG. 1.
Figure 3B:
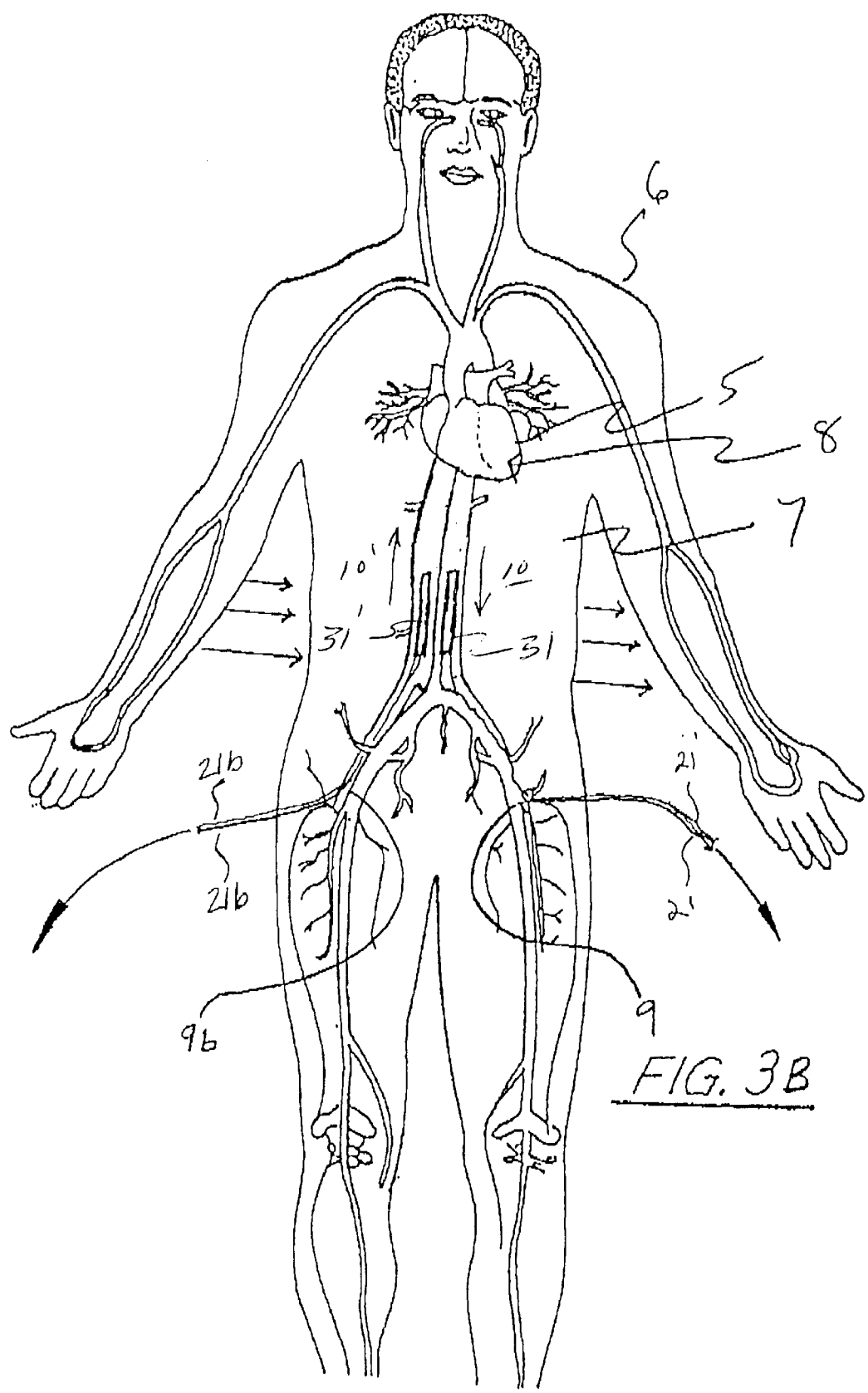
FIG. 3B is a top, partially cut-away view of an alternative embodiment of the invention of FIG. 3A, illustrating first and second electrode assemblies implanted in the aorta and vena cava of the patient, respectively, and the control wires passing therefrom, out of the patient to be controlled by the CCU of FIG. 1.

Continuing with FIG. 1 of the drawings, the invention I of the current invention is driven by a very high field strength electromagnet, anticipated to have a strength of 5–10 Tesla;

the exemplary embodiment of the electromagnet having a field strength of, for example, about 7 Tesla, and utilizing a superconducting magnet 25 having a proven design such as, for example, a Niobium-Titanium, copper stabilized conductor, the magnet having a north, first 26 and a south, second 27 poles driving a magnetic field 30 from the first pole to the second pole, with a space 28 formed therebetween to fit the torso 29 of a patient 6 to be treated. It is iterated that the orientation of the magnetic poles as shown in FIG. 1, and as indicated above, is necessary for the present system to work as described herein. Ideally, such a magnet would have a "persistent switch" in its design to permit it to operate at full field for literally months at a time without the need for recharging.

As shown, the electromagnet 26 is mounted to a base B having a platform 1 having a top side 2 suitable to form a generally horizontal support for the patient, the platform further having first 3 and second 4 ends, configured to support the head and feet of the patient, respectively.

Continuing with FIGS. 1, 2, and 3A, 4A–4C, the first embodiment of the present invention comprises an MHD LVAD (left ventricular assist device) configured to provide assistance to the heart 5 of the patient 6 via assist of the left ventricle 8, wherein an aortic electrode assembly 31 is placed into the abdominal aorta 7 of the patient via the femoral artery 9, the placement in similar fashion to the technique employed in facilitating a balloon angioplasty, as will be more fully explained infra.

The aortic electrode assembly 31 comprises a first 13, anterior electrode and a second 14, posterior electrode, the first 13 and second 14 electrodes configured to engage the inner diameter anterior and posterior, or upper and inner walls 7' of the blood vessel in which they are placed, in this case, the aorta 7 (with the patient laying on their back in a generally horizontal position). In the exemplary aortic electrode assembly 31, the first and second electrodes are held in parallel, spaced 33 relationship at opposing anterior and posterior walls of the blood vessel via a spreader assembly , which may comprise, for example, spring wire supports at the first end 34 of the electrodes, configured to allow for the electrodes to be held in a collapsed condition against one another for insertion, and to spread the electrodes against opposing inner walls of the blood vessel as shown once in the operating position.

Continuing with the Figures, each electrode has a length 15, a width 16, and ideally has concave 20 inner walls 17, 17' and convex outer walls 18, 18', so that the outer walls 18, 18' best engage the radial inner wall 7' of the blood vessel, and to provide the least obstructed, maximum passage of blood 11 therebetween.

Ideally, the total electrode surface area should comprise ⅓–¾+ of the inner diameter 19 surface area of the blood vessel in which it is placed, for maximum efficiency. The electrodes, and all materials utilized in the vicinity of the patient, should be formed of non-magnetic materials to avoid problems due to the very powerful magnetic field generated by the electromagnet 26. For example, the electrodes may be formed of certain non-metallic grades of stainless steel, or gold plated copper or the like.

The first and electrodes would have about the same dimensions, with the concave portions facing one another, and would measure, as an example, 2 centimeters by 10 centimeters.

Control wires 21, 21' communicate with the anterior 13 and posterior 14 electrodes, respectively, the control wires bundled 14 to a computer control unit (CCU) 22. The control wires could be twisted in an effort to eliminate unwanted voltages induced by the large external magnetic field whenever the pump current is changed Sensors 23 which may include Left Ventricular ECG (electrocardiogram), aortic blood flow measurement, blood gas content, including oxygen content, pulmonary pressure, pulmonary blood flow, right ventricular ECG, and the like may be provided, which likewise would feed into the CCU 22. Information from the sensors 23 may be utilized to control the pumping action of the present invention, as will be more fully explained infra.

In use as a LVAD, an incision 37 is made in the femoral artery 9 of the patient, and the aortic electrode assembly 31, in its collapsed 38 state (i.e., the first and second electrodes pressed against one another) is urged into the femoral artery 9 (see FIG. 5), and up 40 into the region of the abdominal aorta 7, where the aortic electrode assembly 31 is positioned such that the first electrode 13 is oriented in anterior fashion relative to the patient, who is in a generally horizontal position on his back in the present example (FIG. 1), with the second electrode 14 positioned in a posterior fashion, with the first and second electrodes spread apart in generally parallel fashion, such that the first and second electrodes communicate with the anterior and posterior inner wall portions of the abdominal aorta, as shown in FIGS. 4A, 4B, and 4C. As in FIG. 1, the patient 6 is positioned such that the magnetic field 30, and associated lines of flux are orthogonal to the blood flow, with said magnetic field running through the blood 11 situated between the first 13 and second 14 electrodes.

Continuing with FIGS. 1, 2, 3, 4A–4C, to initiate blood flow, direct current flow is initiated to the electrodes via the control wires 21, 21', with a positive flow directed to the first, anterior electrode 13 (making the first electrode the anode), and a negative flow directed to the second, posterior electrode 14 (making the second electrode the cathode), thereby sending said D.C. current 37 through the blood 11 between the electrodes 13, 14. By directing the current through the blood 11, the blood between the electrodes 13, 14 is electrified (as blood is a conductor) and, because the electrified blood is simultaneously subject to orthogonal lines of flux from a high magnetic field 30, the electrified blood is subject to hydrodynamic pressures, in accordance with accepted MHD theory, discussed supra, and thereby urged to flow 10 toward the feet of the patient.

In the present example, the magnetic field strength remains about the same. However, by varying the current input to the electrodes, the hydrodynamic pressures, and thereby force of pumping, of the electrified blood between the electrodes can vary considerably, as will be further discussed below.

Figure 4D:
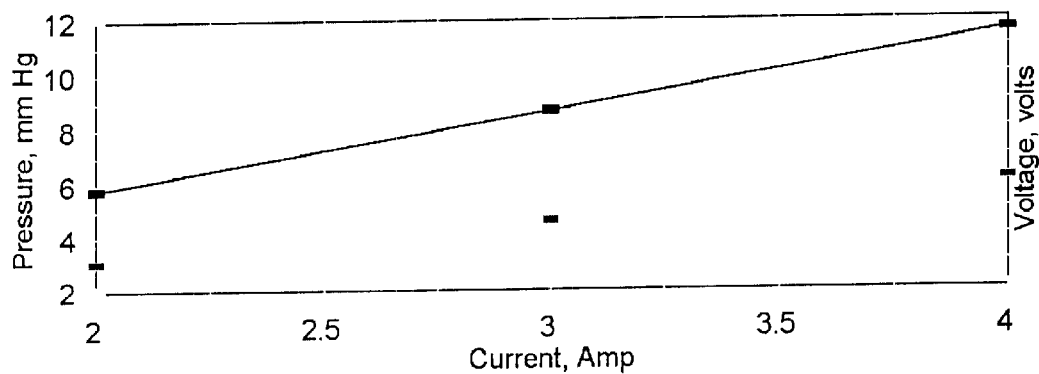
FIG. 4D is a table indicating estimated current and voltage input into an exemplary electrode array having a size comparable to the exemplary electrodes employed in the present invention, and anticipated pumping pressure in an MHD drive scenario with a 7 Tesla magnet, pumping Ringers Solution.
Figure 4E:
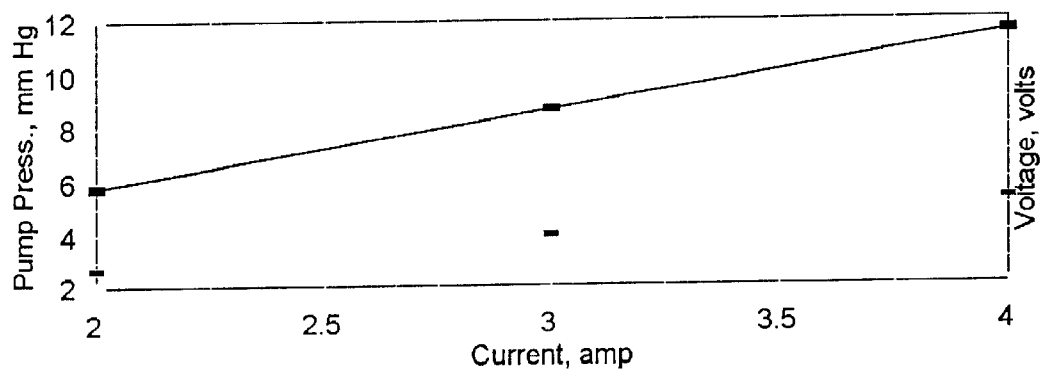
FIG. 4E is a table indicating estimated current and voltage input into an exemplary electrode array having a size comparable to the exemplary electrodes employed in the present invention, and anticipated pumping pressure in an MHD drive scenario with a 7 Tesla magnet, pumping Saline Solution.

In the present scenario, for example, it is estimated that a voltage of six volts, four amps D.C. employed in the aortic electrode assembly in the manner taught above, in a 7 Tesla field, and the first and second electrodes each measuring about 2 centimeters by 10 centimeters, will provide a pumping pressure of about 12 mmHg, although the current, and associated pumping pressure, can vary considerably depending upon the magnetic field strength and induced electrode current from the CCU. This is illustrated in FIGS. 4D and 4E, which set forth approximate pressures for an electrode array similar in size to the present invention, in a 7 Tesla magnetic field, for Ringers Solution and Saline, respectively, which are believed to have conductivity characteristics similar to that of human blood.

A great feature of the present invention is that one can instantly vary the hydrodynamic pumping force of the system by varying the current sent to the electrodes. This is particularly advantageous, as indicated earlier, when one considers that the superconducting magnet, with a perpetual switch, will stay energized, and at about the same field strength, for up to months at a time, and it would generally be less desirable to vary the magnetic field to vary the pumping action. Thus, in the present system, as touched upon supra, the computer control unit (CCU) can utilize ECG and other sensor data so as to vary the current to the electrodes to mimic the pumping of a healthy heart in rhythm with the patient's heart.

As shown in FIGS. 1 and 7, sensors monitoring the ECG, aortic pressure, and aortic blood flow communicate same back to the CCU which analyzes the data and compares same to a comparable healthy heart. Utilizing this data, the CCU can calculate an optimal waveform for current flow to the electrodes to induce hydrodynamic pumping of the blood between the electrodes, so as to mimic the pumping of a healthy heart, thereby providing life support to the patient and reducing the strain upon the damaged heart, all with nominally invasive electrode installation.

As an example, in FIG. 7, the electrical activity 48 is monitored as an ECG line, indicating heart activity 47. Associated with said activity is blood pressure 49 and blood flow 50 wave forms indicating the patient's pressure 44 and flow 41 readings associated with EKG. For comparison, a healthy patients waveform for pressure 46 and flow 43 is superimposed thereupon.

Utilizing this data, the CCU calculates the appropriate blood pressure and flow for the patient, the appropriate current waveform to the electrodes to accomplish same, and sends said current waveform to the electrodes via the control wires (21, 21' in FIG. 5), the first, anterior electrode (13 in FIG. 4B) receiving the positive current, said positive current passing from said first, anterior electrode, through the blood (11 in FIG. 4B) between the electrodes, and to the second, anterior electrode (14 in FIG. 4B).

As indicated, the electrified blood, in conjunction with the indicated orthogonal magnetic field, hydrodynamically motivates said blood between the electrodes along the length of said electrodes, effectively pumping said blood and increasing the patient's blood pressure 45 and blood flow 42 to a level which is considered acceptable for maintaining the patient. For example, the present system, utilized as an LVAD, is expected to hydrodynamically motivate (i.e., "pump") about 4 liters of blood per minute at up to 15 mm Hg, although this figure may vary significantly depending upon the patient, the type of assistance, the condition of the heart, and other criteria.

It is reiterated that this pumping action follows the above wave form, and is not a steady flow, the simulation carried out by the CCU providing a current waveform to the aortic electrode assembly to facilitate the above pumping action to simulate the heart, as set forth in the above wave form. Consequently, the current applied to the electrodes via the CCU has a correlation to the wave forms, with the current rising to peak at the wave peak P, then declining to the next pump cycle, wherein the current (comprising voltage/amperage) again rises to simulate the heart pump, peaking at P', then again declining, and so on.

Continuing with FIGS. 1, 4A and 4B, because the magnetic field runs from the first pole 26 to the second pole 27, and because the first, anterior electrode 13 is positive and the second, posterior electrode 14 is negative, the blood flow 10 facilitated by the MHD effectively streams the blood as a waveform so as to amplify the patient's debilitated heart's pressure and flow (due to the EKG and other monitoring and associated current variance from the CCU) toward the feet of the patient, resulting assistance in pumping of the left ventricle of the heart.

Referring to FIG. 1, it is further indicated that the CCU may include a database 51, or have an network interface 52 to a database, so that it may consult information on accepted blood flow and pressure criteria in its calculations, as well as receive and share diagnostic reference data and operational criteria. Further, the network interface may be utilized by the CCU to communicate information and status on the patient to third parties, or be utilized to access said CCU from a distance for monitoring or control.

Figure 6A:
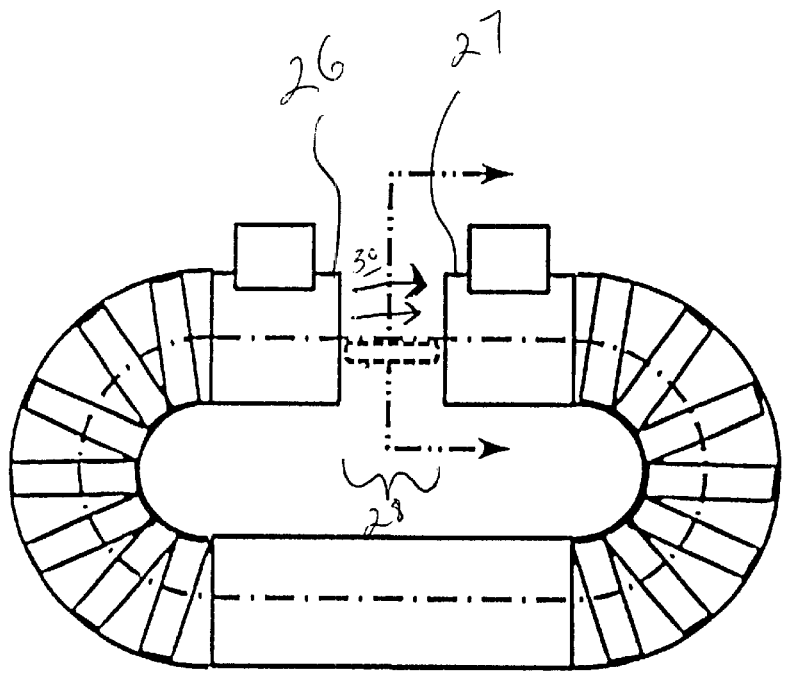
FIG. 6A is an exemplary, cross-sectional view of the exterior magnet of FIG. 1.
Figure 6B:
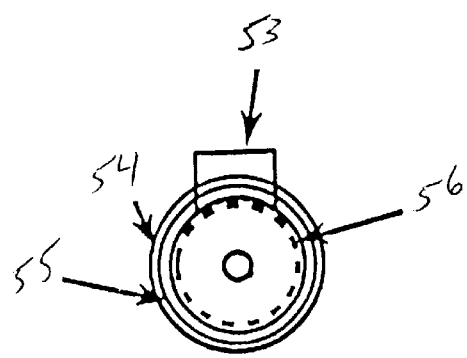
FIG. 6B is an end view of the exterior magnet of FIG. 6A.
Figure 8:
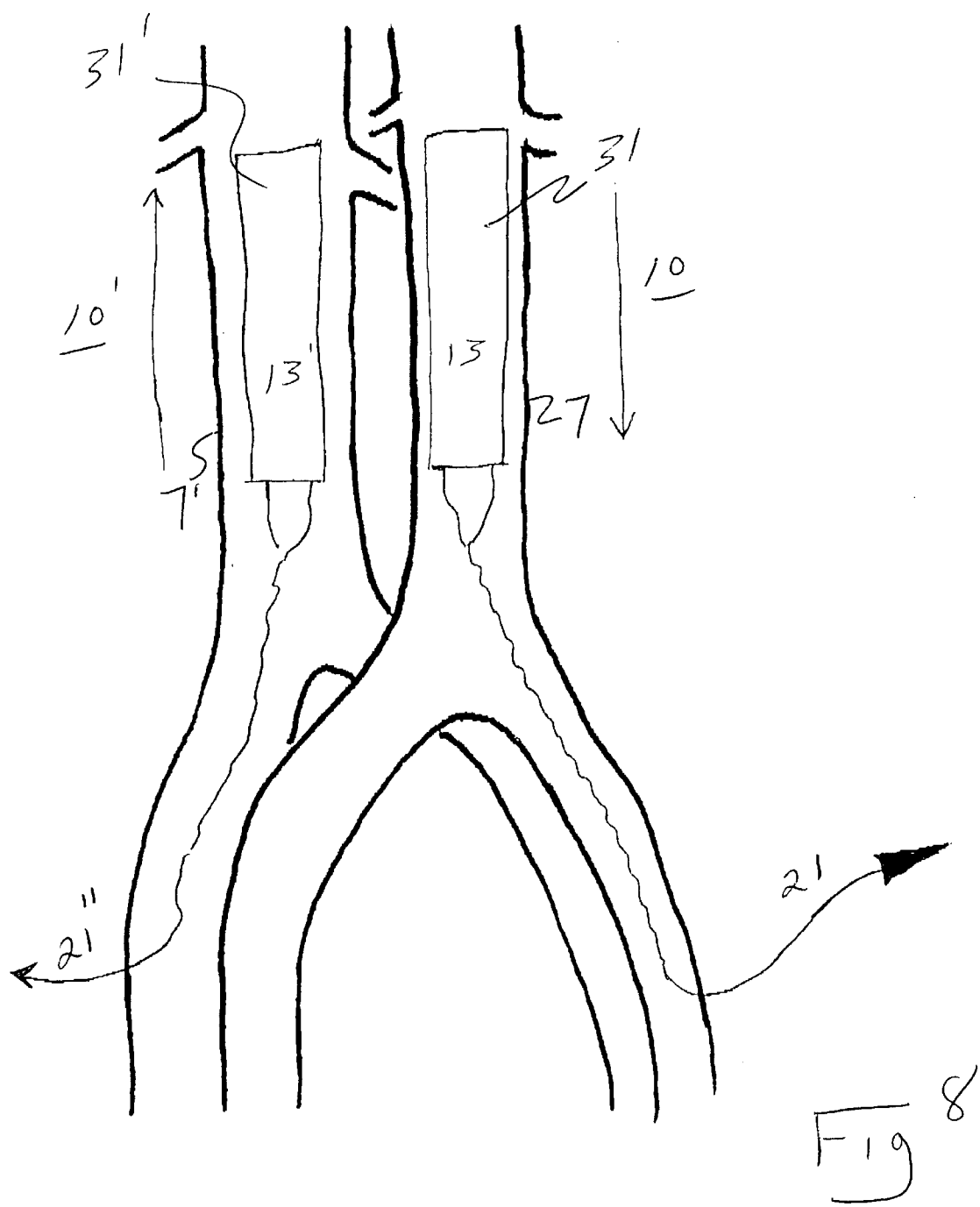
FIG. 8 is a close-up, top, partially cut-away view of the invention of FIG. 3B, illustrating the first and second electrode assemblies implanted in the aorta and vena cava, respectively, and the directions of blood flow therefrom.
Figure 8A:
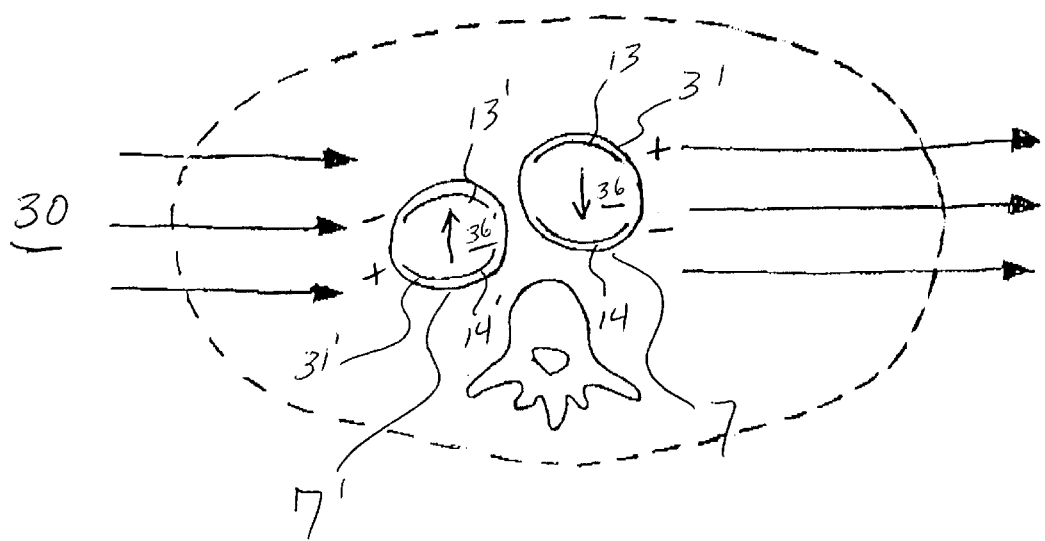
FIG. 8A is a cross-sectional view of the invention of FIG. 8, illustrating the posterior and anterior electrode alignment of the electrode assemblies in the aorta and vena cava, respectively, and the lateral magnetic field traversing therethrough.
Figure 8B:
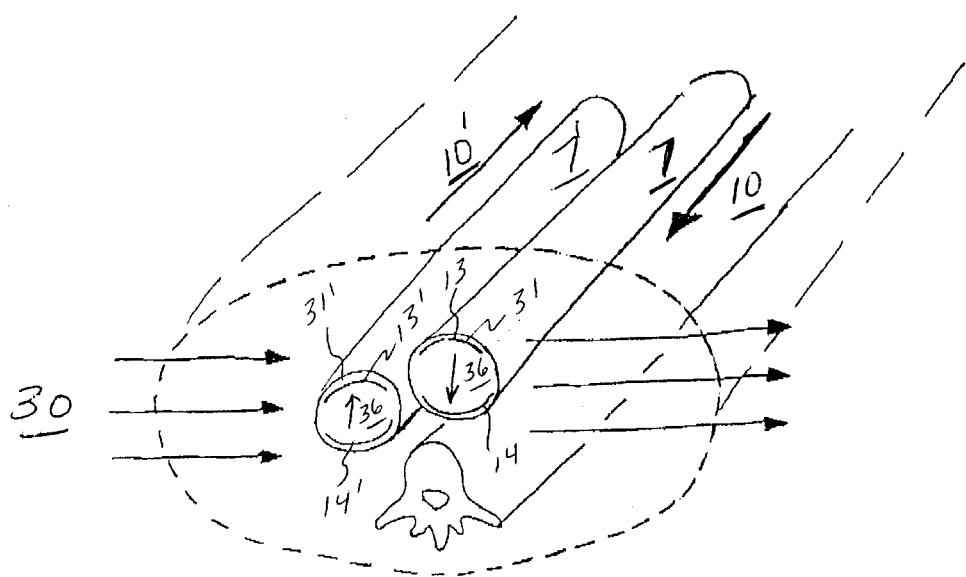
FIG. 8B is an isometric, partially cross-sectional view of the invention of FIG. 8A, illustrating the posterior and anterior electrode alignment of the electrode assemblies in the aorta and vena cava, the blood flow therefrom, and the lateral magnetic field traversing therethrough.

FIGS. 6A and 6B illustrate side and end views, respectively, of an exemplary conceptual design of a superconducting, high field strength magnet which might be utilized in the present invention, although it is iterated that this is only an example, and other designs (including some currently operating) could prove suitable for use in the present invention.

As discussed, the magnet need not be re-invented, and may utilize existing designs and materials, such as a Niobium-Titanium superconducting magnet utilizing a copper stabilized conductor, the magnet having a north, first 26 and a south, second 27 poles driving a magnetic field 30 from the first pole to the second pole, with a space 28 formed therebetween to fit the torso of a patient to be treated. The curved sections of the magnet may be fashioned from identical spools of conductor wound in the same direction, and connected in series. Straight sections are made up of a single spool of conductor, wound in one direction, and connected, along with the curved section spools, in series.

As shown, access panels 53 may be provided to contain vacuum, nitrogen coolant, and helium coolant access lines, as well as retractable power leads and the persistent switch. The winding outer level is surrounded by an LN2 thermal shield and vacuum vessel. Exemplary specifications are as follows:

Winding Bobbin Diameter: 1 Meter

Central Gap: 0.8 meter;

Vacuum Vessel Diameter: 1.3 meters (excluding service stacks);

Maximum field gap at center: 6.5+Tesla

CARDIO BYPASS SYSTEM EMBODIMENT

Continuing with FIGS. 3B, 8, 8A, 8B, and 8C, a second embodiment of the invention is configured to provide a minimally invasive by-pass pump for coronary artery by-pass surgery. With the aortic electrode assembly 31 in the abdominal aorta, as discussed supra, providing a magneto-hydrodynamic motive force (blood flow) away from the heart, a venal electrode assembly 31' having similar elements and design configuration, and placed in the inferior vena cava 7' of the abdomen, but with the posterior electrode 14' having positive polarity D.C. current, and the anterior electrode 13' being negative, (i.e., the electrodes polarity is opposite those of the aortic electrode assembly 31, which anterior 13 electrode was positive and posterior electrode 14 was negative, with current 36 going from top to bottom) thereby hydrodynamically directing the blood flow 10' toward the heart. With the aortic electrode assembly 31 in the Aorta 7, and the venal electrode assembly in the Vena Cava 7' both electrodes energized and independently controllable via control wires 21" to the CCU in a manner similar to that discussed above, complete cardiac pumping action may be taken over for the heart just as it is currently done with a heart by-pass machine, but without the major opening of the chest cavity.

As indicated, in contrast with current coronary by-pass procedures, in the present system establishes artificial circulation without opening the chest cavity. The aortic electrode assembly 31 and the venal electrode assembly 31' are inserted through major blood vessel (s) such as the femoral artery and vein, respectively, then said electrodes are advanced into the aorta 7 and inferior vena cava 7', respectively. As indicated, the polarity of each electrode assembly will be such that the aortic electrode assembly facilitates flow in the aorta away from the heart 10 and the venal electrode assembly facilitates flow in the inferior vena cava has flow 10' toward the heart (Anterior electrode is negative, posterior electrode is positive), The aortic and venal electrode assemblies should be oriented in generally parallel configuration, and situated generally along the same plane.

Once the magnetohydrodynamic flow is in effect, the patients heart may be stopped, and much less invasive procedures can occur to repair coronary blood vessels such as through an endoscope, as discussed.

It is anticipated that the dimensions of the electrodes forming the venal electrode assembly 13' for use in the inferior vena cava will be about the same as the aortic electrode assembly, as employed in the aorta, above, although the operating current and pressures may be slightly different. The venal electrode assembly, urging blood to the right ventricle of the heart, must also urge the blood through the lungs as pulmonary circulation before returning to the left ventricle of the heart.

Accordingly, it is anticipated that the venal electrode assembly 13' will not have as great a pressure head as the aortic electrode assembly 13 in the aorta, so the operating voltage may be less for the venal electrode assembly.

For example, 5.5 volts D.C. at 3.5 amps, producing an anticipated pressure of 10 Hg; this is simply an estimate utilizing an electrodes forming the venal electrode assembly the same size as those employed in the aortic electrode assembly 31, although these estimates may vary considerably when the system is actually put into practice on a living being.

In utilization for a bypass, once the first and second electrode assemblies are installed into the aorta and inferior vena cava, respectively, as discussed, and the patient positioned such that the electromagnetic field lines (of adequate strength, for example 7–10 Tesla) pass through the torso of the patient and orthogonal to and through the blood situated between the anterior and posterior electrodes of the first and second electrodes; sensors (23' in FIG. 1) on the patient are employed for sensing, pulmonary pressure, vena cava pressure and blood flow, pulmonary oxygenation, aortic pressure and blood flow and others are used for feedback in controlling the current wave forms sent to the first and second electrode assemblies, respectively.

Once the heart is stopped, the CCU (FIG. 1) sends a current wave form to the first and second electrode assemblies so as to provide pumping in the artificial wave form to simulate that of the stopped heart, as shown in FIG. 9, the aortic blood flow 62 facilitated by the aortic electrode assembly in the aorta, the pulmonary artery blood flow facilitated by the venal electrode assembly in the inferior vena cava.

With artificial circulation established, the surgeon operate on the heart utilizing endoscopic or other minimally invasive surgery, and re-start the heart once complete.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A cardiac assist device for a patient having an aorta having an inner diameter, the aorta filled with blood, comprising:

an electrode assembly, said electrode assembly having an uncollapsed configuration wherein said first and second electrodes are situated in spaced relationship so as to permit the accumulation and passage of blood therebetween while said electrode assembly is situated within the aorta said electrode assembly having a collapsed configuration wherein said first and second electrodes are situated adjacent to one another so as to facilitate the insertion of said electrode assembly into the aorta;

a direct current power supply for supplying power to said first and second electrodes, said direct current power supply producing a current flow from said first electrode so as to electrify blood situated between said first and second electrodes, producing electrified blood, said current flow passing on to said second electrode;

a magnet for providing a magnetic field so as to produce lines of flux which pass through said blood situated between said first and second electrodes, said lines of flux being orthogonal to said current flow;

said magnetic field interacting with said electrified blood so as to produce a magnetohydrodynamic flow of said electrified blood, said flow running at a right angle to said lines of flux and said current flow.

2. The cardiac assist device of claim 1, wherein said first and second electrodes are situated within said the aorta adjacent to opposing sides of the inner diameter of the aorta, to facilitate maximum passage of blood therebetween.

3. The cardiac assist device of claim 2, wherein said first electrode forms a anterior, anode electrode, and wherein said second electrode forms a posterior, cathode electrode.

4. The cardiac assist device of claim 3, wherein there is provided a computer control unit to vary current flow to said first and second electrodes forming said aortic electrode assembly, so as to the simulate pumping action of a heart.

5. The cardiac assist device of claim 4, wherein there is further provided sensor means for sensing the condition of the patient, said sensor means utilized by said computer control unit to vary the current flow in simulating the pumping action of the patient's heart.

6. The cardiac assist device of claim 5, wherein said sensor means comprises ECG, blood oxygen levels, blood pressure and blood flow sensors on the patient.

7. The cardiac assist device of claim 6, wherein said computer control unit utilizes ECG information from said ECG sensor to calculate a current wave form for said electrode assembly, so as to facilitate magnetohydrodynamic pumping of the blood between said first and second electrodes.

8. The cardiac assist device of claim 1, wherein said magnetic field is between 5–10 Tesla.

9. A cardiac bypass pump device for a patient having an aorta having an inner diameter, an inferior vena cava having an inner diameter, the inferior vena cava and aorta filled with blood, comprising:

an aortic electrode assembly, said aortic electrode assembly having an uncollapsed configuration wherein said first and second electrodes are situated in spaced relationship so as to permit the accumulation and passage of blood therebetween while said aortic electrode assembly is situated within the aorta said electrode assembly having a collapsed configuration wherein said first and second electrodes are situated adjacent to one another so as to facilitate the insertion of said aortic electrode assembly into the aorta;

a direct current power supply for supplying power to said first and second electrodes of said aortic electrode assembly, said direct current power supply producing an aortic current flow from said first electrode so as to electrify blood situated between said first and second electrode of said aortic electrode assembly, producing electrified blood, said aortic current flow passing on to said second electrode;

a venal electrode assembly, said venal electrode assembly having an uncollapsed configuration wherein said first and second electrodes are situated in spaced relationship so as to permit the accumulation and passage to of blood therebetween while said venal electrode assembly is situated within the vena cava said electrode assembly having a collapsed configuration wherein said first and second electrodes are situated adjacent to one another so as to facilitate the insertion of said venal electrode assembly into the inferior vena cava;

a direct current power supply for supplying power to said first and second electrodes of said venal electrode assembly, said direct current power supply producing a venal current flow from said second electrode of said venal electrode assembly so as to electrify blood situated between said first and second electrodes of said venal electrode assembly, producing electrified blood, said venal current flow passing on to said first electrode;

means for providing a magnetic field so as to produce lines of flux which pass through blood situated between said first and second electrodes of said aortic electrode assembly, and said first and second electrodes of said venal electrode assembly, said lines of flux being orthogonal to said aortic and venal current flows.

10. The cardiac assist device of claim 9, wherein said first and second electrodes of said aortic electrode assembly communicate with opposing sides of the inner diameter of the aorta, so as to facilitate maximum passage of blood therebetween, and said first and second electrodes of said venal electrode assembly communicate with opposing sides of the inner diameter of the inferior vena cava, so as to facilitate maximum passage of blood therebetween.

11. The cardiac assist device of claim 10, wherein said first electrode of said aortic electrode assembly forms a anterior, anode electrode, wherein said second electrode of said aortic electrode assembly forms a posterior, cathode electrode, and wherein said first electrode of said venal electrode assembly forms an anterior, cathode electrode, and wherein said second electrode of said venal electrode assembly forms a posterior, anode electrode.

12. The cardiac assist device of claim 11, wherein there is provided a computer control unit to vary current flow to said aortic and venal electrode assemblies, so as to the simulate pumping action of a heart.

13. The cardiac assist device of claim 12, wherein there is further provided sensor means for sensing the condition of the patient, said sensor means utilized by said computer control unit to vary the current flow in simulating the pumping action of the patient's heart.

14. The cardiac assist device of claim 13, wherein said sensor means comprises ECG, blood oxygen levels, blood pressure and blood flow sensors on the patient.

15. The cardiac assist device of claim 14, wherein said computer control unit utilizes ECG information from said ECG sensor to calculate a current wave form for said aortic and venal electrode assemblies, so as to facilitate magnetohydrodynamic pumping of the blood within said aortic and venal electrode assemblies.

16. The cardiac assist device of claim 15, wherein said magnetic field is between 5–10 Tesla.

17. The method of facilitating circulation of blood in a blood vessel in a patient, comprising the steps of:
   a) providing a collapsible electrode assembly, said electrode assembly having first and second electrodes situated in opposing, spaced relationship adjacent to the inner wall of said blood vessel to facilitate the accumulation and passage of blood therebetween when in an uncollapsed state;
   b) urging said first and second electrodes toward one another, providing a collapsed electrode assembly;
   c) inserting said collapsed electrode into said blood vessel, providing an inserted electrode assembly;
   d) allowing said first and second electrodes in said inserted electrode assembly be urged to an uncollapsed state within the blood vessel, wherein said first and second electrodes are situated in a generally parallel, spaced relationship;
   e) passing a direct current flow from said first electrode, through blood situated between said first and second electrodes, to said second electrode, forming electrified blood;
   f) providing a magnetic field driven through said blood vessel, said magnetic field producing lines of flux which pass through the blood situated between said first and second electrodes forming said electrode assembly, said lines of flux being orthogonal to said current flow;
   g) allowing said magnetic field to interact with said electrified blood so as to produce a magnetohydrodynamic flow of said electrified blood, said flow running at a right angle to said lines of flux and said current flow.

18. The method of claim 17, wherein there is further provided the step of sensing the condition of the patient, providing sensor information, and utilizing said sensor information to vary the current flow to said electrode assembly, so as to optimize blood flow.

19. A device for promoting fluid movement in a fluid conduit having an inner wall forming an interior having fluid situated therein, comprising:
   an electrode assembly adapted to be situated in the interior of said conduit said electrode assembly having an uncollapsed configuration wherein said first and second electrodes are situated in spaced relationship so as to permit the accumulation and passage of fluid therebetween while said electrode assembly is situated within the conduit, said electrode assembly having a collapsed configuration wherein said first and second electrodes are situated adjacent to one another so as to facilitate the insertion of said electrode assembly into the conduit;
   a power supply for supplying power to said first and second electrodes, said power supply producing a current flow between said first and second electrodes to electrify fluid situated between said first and second electrode, so as to produce electrified fluid;
   a magnet for providing a magnetic field to produce lines of flux which pass through said fluid situated between said first and second electrodes, said lines of flux being orthogonal to said current flow;

said magnetic field interacting with said electrified fluid to produce a magnetohydrodynamic flow of said electrified fluid within the conduit.

20. A cardiac assist device for a patient having a blood vessel having an inner wall having an interior having blood situated therein, comprising:

an electrode assembly formed for insertion into the interior of the blood vessel, said electrode assembly having first and second electrodes situated in generally parallel, spaced relationship so as to permit the passage of blood therebetween, said electrode assembly being collapsable to facilitate the urging of said first and second electrodes toward one another, providing a collapsed electrode so as to facilitate the insertion of said collapsed electrode into said blood vessel;

a power supply for supplying power to said first and second electrodes, said power supply producing a current flow through blood situated between said first and second electrodes, producing electrified blood;

means for producing a magnetic field orthogonal to said current flow, so as to produce a magnetohydrodynamic flow of said electrified blood.

21. The cardiac assist device of claim 20, wherein the inner wall of the blood vessel is radial and said first and second electrodes are radially configured to engage opposing sides of the inner diameter of the blood vessel, to facilitate maximum passage of blood therebetween.

22. The cardiac assist device of claim 21, wherein said first electrode forms a anterior, anode electrode, and wherein said second electrode forms a posterior, cathode electrode.

23. The cardiac assist device of claim 22, wherein there is provided a computer control unit to vary current flow to said first and second electrodes forming said aortic electrode assembly, so as to the simulate pumping action of a heart.

24. The cardiac assist device of claim 23, wherein there is further provided sensor means for sensing the condition of the patient, said sensor means utilized by said computer control unit to vary the current flow in simulating the pumping action of the patient's heart.

25. The cardiac assist device of claim 24, wherein said sensor means comprises ECG, blood oxygen levels, blood pressure and blood flow sensors on the patient.

26. The cardiac assist device of claim 25, wherein said computer control unit utilizes ECG information from said ECG sensor to calculate a current wave form for said electrode assembly, so as to facilitate magnetohydrodynamic pumping of the blood between said first and second electrodes.

27. The cardiac assist device of claim 20, wherein said magnetic field is between 5–10 Tesla.

28. A cardiac assist device for a patient having a blood vessel having blood situated therein, comprising:

an electrode assembly adapted to be situated in the blood vessel, said electrode assembly having an uncollapsed configuration wherein said first and second electrodes are situated in spaced relationship so as to permit the accumulation and passage of blood therebetween while said electrode assembly is situated within the blood vessel, said electrode assembly having a collapsed configuration wherein said first and second electrodes are situated adjacent to one another so as to facilitate the insertion of said electrode assembly into the blood vessel;

a power supply for supplying power to said first and second electrodes, said power supply producing a current flow through blood situated between said first and second electrodes, producing electrified blood;

means for producing a magnetic field orthogonal to said current flow, so as to produce a magnetohydrodynamic flow of said electrified blood in such a manner as to facilitate the flow of blood through the blood vessel.

29. The cardiac assist device of claim 28, wherein said first and second electrodes are adapted to communicate with opposing sides of the inner diameter of the blood vessel, so as to facilitate maximum passage of blood therebetween.

30. The cardiac assist device of claim 29, wherein there is provided a computer control unit to vary current flow to said first and second electrodes forming said aortic electrode assembly, so as to the simulate pumping action of a heart.

31. The cardiac assist device of claim 30, wherein there is further provided sensor means for sensing the condition of the patient, said sensor means utilized by said computer control unit to vary the current flow in simulating the pumping action of the patient's heart.

32. The cardiac assist device of claim 31, wherein said sensor means comprises ECG, blood oxygen levels, blood pressure and blood flow sensors on the patient.

33. The cardiac assist device of claim 32, wherein said computer control unit utilizes ECG information from said ECG sensor to calculate a current wave form for said electrode assembly, so as to facilitate magnetohydrodynamic pumping of the blood between said first and second electrodes.

34. The cardiac assist device of claim 33, wherein said magnetic field is between 5–10 Tesla.

35. The method of facilitating circulation of blood in a patient, comprising the steps of:

a) providing an electrode assembly having first and second electrodes situated in generally parallel, spaced relationship;

b) urging said first and second electrodes towards one another, providing a collapsed electrode;

c) inserting said collapsed electrode into a blood vessel;

d) allowing said first and second electrodes of said collapsed electrode to be urged in an uncollapsed state within the blood vessel, such that said first and second electrodes are situated in a generally parallel, spaced relationship within the blood vessel of the patient, so as to permit the accumulation and passage of blood therebetween;

e) passing a direct current flow from said first electrode, through blood situated between said first and second electrodes, to said second electrode, forming electrified blood;

f) providing a magnetic field orthogonal to said current flow and through said electrified blood;

g) allowing said magnetic field to interact with said electrified blood so as to produce a magnetohydrodynamic flow of said electrified blood, said flow running at a right angle to said lines of flux and said current flow.

36. A fluid pump for facilitating the flow of fluid though a blood vessel, comprising:

a collapsible electrode assembly adapted to be inserted within said blood vessel, said electrode assembly having first and second electrodes situated in generally parallel, spaced relationship so as to permit the passage of fluid situated therebetween;

a power supply for supplying power to said first and second electrodes so as to produce a current flow through fluid between said first and second electrodes;

a magnet for providing a magnetic field orthogonal to said current flow;

said magnetic field interacting with said electrified fluid so as to produce a magnetohydrodynamic flow of fluid between said first and second electrodes and through said blood vessel.

* * * * *